(12) United States Patent
Jalonen et al.

(10) Patent No.: US 7,187,178 B2
(45) Date of Patent: Mar. 6, 2007

(54) METHOD FOR DETERMINING THE VOLTAGE SENSITIVITY OF THE DISTANCE BETWEEN THE MIRRORS OF A FABRY-PEROT INTERFEROMETER

(75) Inventors: Marko Jalonen, Vantaa (FI); Niina Hakkarainen, Espoo (FI); Matti Kokki, Vantaa (FI)

(73) Assignee: Vaisala Oyj, Helsinki (FI)

( * ) Notice: Subject to any disclaimer, the term of this patent is extended or adjusted under 35 U.S.C. 154(b) by 0 days.

(21) Appl. No.: 10/548,596

(22) PCT Filed: Mar. 24, 2004

(86) PCT No.: PCT/FI2004/000165

§ 371 (c)(1),
(2), (4) Date: Sep. 13, 2005

(87) PCT Pub. No.: WO2004/085979

PCT Pub. Date: Oct. 7, 2004

(65) Prior Publication Data

US 2006/0164095 A1    Jul. 27, 2006

(30) Foreign Application Priority Data

Mar. 24, 2003 (FI) .................................. 20030430

(51) Int. Cl.
G01N 27/62 (2006.01)
G01N 35/00 (2006.01)
G01B 9/02 (2006.01)
(52) U.S. Cl. .................. 324/464; 73/1.07; 356/519
(58) Field of Classification Search ................. 73/1.07; 356/517, 519, 480

See application file for complete search history.

(56) References Cited

U.S. PATENT DOCUMENTS

| 4,685,325 | A  | * | 8/1987  | Warchol ................. 73/19.07 |
| 5,172,185 | A  | * | 12/1992 | Leuchs et al. ............. 356/482 |
| 5,218,426 | A  | * | 6/1993  | Hall et al. ................. 356/517 |
| 5,550,373 | A  |   | 8/1996  | Cole et al. |
| 6,842,254 | B2 | * | 1/2005  | Van Neste et al. .......... 356/497 |
| 6,842,256 | B2 | * | 1/2005  | Hill ......................... 356/517 |
| 2002/0061042 | A1 |   | 5/2002 | Wang et al. |

FOREIGN PATENT DOCUMENTS

| EP | 0 753 733 A1 | 1/1997 |
| EP | 1 204 181 A3 | 5/2002 |

* cited by examiner

*Primary Examiner*—Andrew H. Hirshfeld
*Assistant Examiner*—Jeff Natalini
(74) *Attorney, Agent, or Firm*—Birch, Stewart, Kolasch & Birch, LLP

(57) ABSTRACT

A method for determining the voltage sensitivity of the distance between the mirrors of a Fabry-Perot interferometer in a measuring device, which is intended to measure a predefined gas (CO2), of which at least one absorption maximum or minimum is known. At least two calibration point are defined device specifically using a reference gas (N2) in controlled conditions. A 'virtual' signal-control-voltage sensitivity curve, is formed with the aid of the calibration points formed using the reference gas (N2), ratios of the measurement points of the predefined gas (CO2) and of the corresponding values of the reference-gas curve are formed, and at least one voltage value corresponding to the minimum or maximum is defined from the ratios, in which case, on the basis of the wavelengths of the absorption minima or maxima of the gases (CO2, N2) being measured, the voltage sensitivity of the distance between the mirrors can be defined unequivocally.

19 Claims, 2 Drawing Sheets

METHOD FOR DETERMINING THE VOLTAGE SENSITIVITY OF THE DISTANCE BETWEEN THE MIRRORS OF A FABRY-PEROT INTERFEROMETER

CROSS-REFERENCE TO RELATED APPLICATION

The present application claims priority under 35 U.S.C. §119 to International Application No. PCT/FI 2004/000165, filed Mar. 24, 2004, the entire contents of which are hereby incorporated by reference.

BACKGROUND OF THE INVENTION

1. Field of the Invention

The present invention relates to a method for determining the voltage sensitivity of the distance between the mirrors of a Fabry-Perot interferometer. The invention also relates to a computer-software product for implementing the method.

2. Description of Background Art

Electrically adjustable Fabry-Perot interferometers (FPI) are commonly used as adjustable band-pass filters in, among other things, optical content measurements. The use of this method achieves considerable improvements in performance and especially in long-term stability. The use of the method according to the invention permits the control-voltage sensitivity of the distance between the mirrors of an FPI band-pass filter to be determined precisely, thus further improving the measurement accuracy of FPI technology.

For example, the long-term stability of the measurement of carbon dioxide ($CO_2$) is based on measuring two wavelength bands in a single channel, an absorption band (ABS 4.26 μm) and a reference band (REF 3.9 μm). These two bands are typically selected using an adjustable micro-mechanical optical FPI band-pass filter, the pass band of which can be selected using voltage. The FPI control voltages corresponding to these bands are marked Vabs and Vref. The content, or a quantity proportional to it is calculated on the basis of the ratio (Tx/Rx) of the signals received from these two bands, i.e. the Tx signal value is measured using the Vabs voltage and the Rx correspondingly using the Vref voltage.

For example, the first equivalent condition for the stability of a carbon-dioxide transmitter is for the voltage control corresponding to the FPI voltages stored in the memory during factory tuning, i.e. the absorption and reference voltages and the pass bands corresponding to them, to remain unchanged over the short and long terms. For example, instability in the control voltage and rapid changes in temperature may lead to shift in the FPI pass bands and thus cause changes to appear.

SUMMARY AND OBJECTS OF THE INVENTION

The invention is intended to improve the performance of the technology described above and for this purpose to create an entirely new type of method for determining the voltage sensitivity of the distance between the mirrors of a Fabry-Perot interferometer.

The invention is based on recording, in connection with the manufacture of the FPI element, at least two measurement points for the signal-control-voltage sensitivity of a reference gas and defining, with the aid of these points, a 'virtual' reference-gas curve, for example, a straight line. A gas, which essentially does not absorb light in the same selected wavelength band as the gas to be measured, is used as the reference gas. In $CO_2$ measurements, such a reference gas is, for example, $N_2$. If there is a sufficient content of the gas being measured, the signal values of the selected absorption minima and/or maxima in the environment are measured, ratios are formed of these signal values and the corresponding signal values of the reference-gas curve, on the basis of which the natural constants, i.e. control-voltage equivalences of the absorption minima and/or maxima, are defined. This method can be applied particularly in the case of a measurement gas that is typically present in the measurement conditions. For example, the method can be reasonably used in $CO_2$ gas measurements, as $CO_2$ gas is one of the main background gases in the environment.

Considerable advantages are gained with the aid of the invention.

With the aid of the invention, possible wavelength-band drift in the FPI can be detected and eliminated, both effectively and reliably.

The calibration method is reliable, because it is based on the use of natural constants, the real absorption maxima or minima of real gases, so that drift will not occur in the reference values. The control voltage of the electronics and the imperfections of the system's other components are thus eliminated with the aid of unvarying natural constants.

The method in question can be used both in actual gas measurement and during calibration. The manufacture of FPI components can be simplified, as the imperfections of the manufacturing process can be compensated by the calibration procedure.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

DETAILED DESCRIPTION OF THE PREFERRED EMBODIMENTS

A Fabry-Perot interferometer is an optical component, which includes two approximately parallel semi-reflecting mirrors in the path of the signal, the distance between which is adjusted by altering the voltage between the electrodes in the mirrors. The change in the distance between the mirrors changes the pass band of the filter. In this application, the term control voltage is used to refer to precisely the voltage intended to adjust the distance between the mirrors.

This FPI technology is disclosed in, among others, U.S. Pat. Nos. 5,561,523 and 5,646,729.

The basic equation of the Fabry-Perot interferometer is $$2d = n\lambda \quad \quad (1)$$

in which d in the distance between the mirrors of the resonator, n is an integer (=order) and $\lambda$ is the wavelength. The value of the refractive index of the substance between the mirrors is assumed to be unity. In so-called long interferometers, n is usually 100–100,000. The present invention is advantageous in connection with precisely short interferometers, in which n is 1–3. The width of the pass bands of the interferometer B (=FWHM) depends of the reflection coefficient r of the mirrors and on the value of d:

$$B = \frac{1 - r\lambda^2}{\sqrt{r}\, 2\pi d} \quad \quad (2)$$

The free spectral range (FSR) between the different orders refers to the distance between the adjacent pass bands. The FSR can be calculated from equation (2) for the values of n n and n+1:

$$\lambda_n - \lambda_{n+1} = \frac{2d}{n} - \frac{2d}{n+1} = \frac{2d}{n(n+1)} \quad \quad (3)$$

It can be seen from equation (3) that the FSR increases as n diminishes. A large FSR will facilitate the removal of adjacent orders, for example, using a band-pass filter. The value d of an interferometer made using surface micromechanics can be 2.1 µm and n=1. The FSR then receives the value 2.1 µm.

Figure 1:
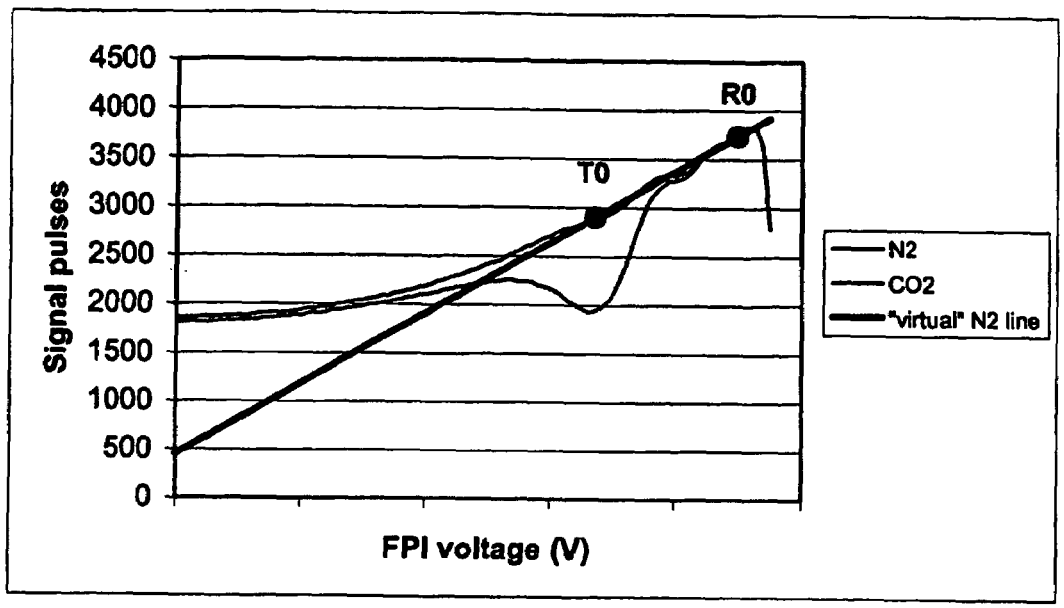
FIG. 1 shows a graphical representation of the data on the FPI's control voltage, used in the method according to the invention, as a function of the signal passing through the FPI.
Figure 2:
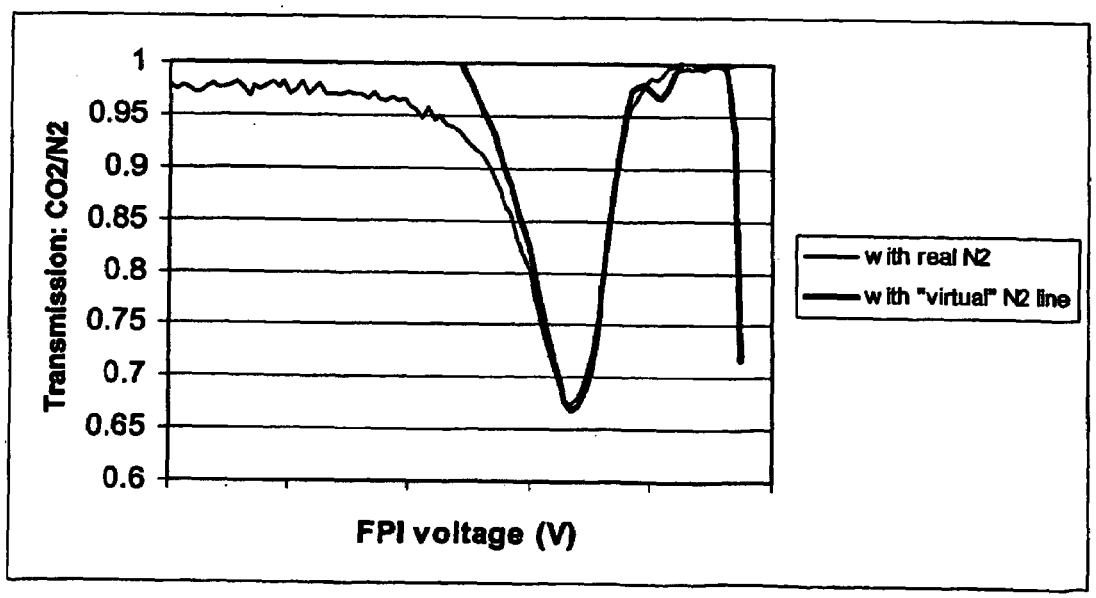
FIG. 2 shows the data of the figure as values in proportion to each other.

The following describes the basic solution according to the invention, according to FIGS. 1 and 2.

To ensure that there will always be a reference curve (e.g., an N2 reference curve) available for analysis, without actually using that gas, a 'virtual' N2 reference curve is formed, i.e. at its simplest, a signal-FPI straight line. This straight line is formed through the calibration values T0 (at Vabs) and R0 (at Vref) of the reference gas (e.g., N2) obtained from the factory calibration and recorded in the memory of the device, according to FIG. 1. Instead of a straight line, it is also possible to use a reference curve formed from several points, which is defined and can be stored in the memory of the devices during the factory calibration. Thus, in factory calibration, the value of the control voltage for the maximum absorption (Vabs) of the gas (in this case, CO2) being measured and correspondingly for the reference voltage (Vref), as well as for the signal values corresponding to them in the reference gas, are determined with the aid of a reference gas (in this base, N2). If necessary, values corresponding to these control-voltage values can also be calculated as the distance between the mirrors. If N2 gas is used, it can be shown that the transmission curve obtained with the aid of the virtual curve corresponds well to the transmission curve close to the Vabs voltage determined with the aid of real N2 gas, according to FIG. 2.

Figure 3:
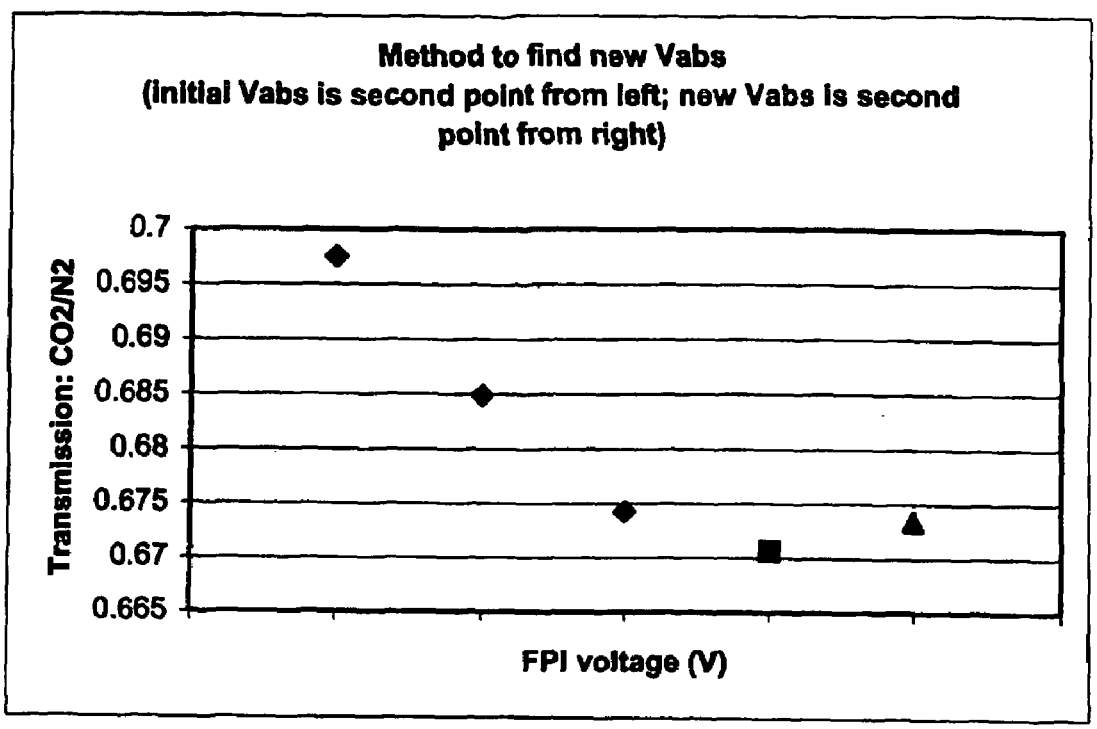
FIG. 3 shows a graphical representation of an example of one absorption-maximum search algorithm according to the invention.

Once a virtual reference curve has been formed, the gas to be measured (e.g., CO2) is measured in the environment of the absorption band (ABS) from the end of the previously agreed control-voltage step and the ratios of the signal values of the gas being measured and of the virtual curve. On the basis of these ratios, a new minimum (FIG. 3) is found, the position of which gives a corrected value (Vabs) for the control voltage corresponding to the absorption maximum of the carbon dioxide. Vref is formed from this value by calculation in a manner to be described later.

In practice, the FPI voltage values (Vabs and Vref) are the newest FPI voltage values. This means that, after the FPI voltage-scale correction according to the method disclosed here, the 'N2 virtual straight line' is also scaled according to the new Vabs and Vref, so that the T0 and R0 values being used will correspond to these new voltage values. The signal values T0 and R0 are always the newest N2 calibration values available.

Various Self-Analysis Procedures

An FPI self-analysis can always be made, according to the performance objectives and available equipment, by applying, for example, some of the following procedures:

1. A continuous automatic alternating cycle of measurements and analysis, with a specific rhythm (e.g., 10/1) i.e., automatically after a cycle of, for example, 10 measurements, one measurement including analysis is made, after which normal measurements are continued. The analysis is continued according to the cycle. The analysis can also be completed at one time, if a rapid response time is not demanded.
2. A specific analysis interval is defined (e.g., hour, day, week, or month), after which analysis is started automatically. The analysis is completed at one time.
3. When condition limits are exceeded (pressure, temperature, RH, etc.).
4. At the user's initiative.
5. Utilizing any of the procedures (1–4) described above, in such a way that the user receives an error report and possible an instruction to correct the control-voltage.
6. Utilizing the procedures (1–4) described above, in such a way that the control-voltage is corrected automatically.

Irrespective of the procedure, the output results during a measurement forming part of the analysis are typically locked to the last measurement value received.

A. Self-Analysis Conditions

In addition, the following conditions, for example, are also required, in order to define a suitable time for analysis and to ensure the reliability of the analysis result. The following conditions can be applied as required:

Because the analysis described requires the gas being measured to be present, a condition is needed for the sufficient content of the gas. This can be presented as an absorption condition, for example Tx/T0<0.95. The values is sensor-type specific.

The analysis cannot be carried out during a pronounced state of change (the content of the gas changes rapidly or the sensor signal is excessively noisy), i.e. the signals being measured must be sufficiently stable: Correction based on the analysis is made only once the stability conditions have been met. Such conditions can be, for example, the following:

Content condition: Tx/Rx (or Tx/T0) must be within specific limits before and after the analysis.

Noise condition: For example, continuous noise measurement alongside the normal measurement, (e.g., 1 min) before and after the analysis. Noise-level must be sufficiently low.

The lower limit to Vabs change in the FPI must be defined (to be, for example, the same as the absorption-voltage step of the analysis), to prevent an increase in output noise, due to continuous very small changes in Vabs.

In addition, an upper limit to the cumulative Vabs correction will be required, which will permit the original Vabs characterization estimate to be made in its entirety.

One analysis can include several analysis cycles, which will ensure that the selected new Vabs really is the new absorption maximum. In addition, an average can be calculated from the new Vabs values obtained. If an average is used, a condition must be set for the divergence of the Vabs found, to ensure reliability.

B. Determining of the FPI Absorption Maximum Voltage (Vabs) of the Measured Gas, According to FIG. 3

A sensor-type-specific voltage step (e.g., 0.2 V) is selected for the self-analysis.

In practice, in addition to the Vabs being used, the voltage point (e.g., Vabs–0.2 V, the left-hand side point in the figure) that is at a distance of one voltage step is selected. The signal value of this point is divided by the value of the corresponding voltage of the N2 virtual straight line. If the ratio obtained is greater than the corresponding ratio calculated in Vabs, the analysis is then continued by calculating a new ratio using the Vabs+0.2 V control voltage (the third point from the left in the figure). If this ratio is also greater than the corresponding ratio calculated in Vabs, the analysis is terminated and the Vabs voltage is not corrected. If the ratio with the control voltage Vabs+0.2 V is smaller than the corresponding ratio calculated in Vabs, as in FIG. 3, the analysis is then continued further to the right in the figure, i.e. the signal value with the control voltage Vabs+0.4 V is measured and the ratio of this and the straight line's corresponding value is calculated as above. The analysis is continued in this way, until a new Vabs is found, i.e. a new FPI control voltage corresponding to the maximum absorption. The sequence of measuring the measurement points in the analysis described above can be changed.

C. Definition of a New FPI Reference Voltage

A new Vref corresponding to the new Vabs is now calculated. The connection between the FPI control voltage and its void interval are derived starting from the equilibrium condition between the electrostatic force and the spring force of the upper mirror. The new Vabs and Vref (or the magnitudes of the corrections made to them) are recorded in the memory and utilized in measurement.

The method according to the invention is typically implemented with the aid of a computer program, in the processor in the equipment.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

The invention claimed is:

1. A method for determining the voltage sensitivity of a distance between the mirrors in a Fabry-Perot interferometer (FPI), which is intended to measure an absorption value of a predefined gas, of which at least one absorption maximum (ABS) or minimum is known, the method including the steps of:

defining at least two device-specific calibration points using a reference gas in controlled conditions, in such a way that at least one of the calibration points (ABS) includes information on a control-voltage signal pair for one absorption maximum (ABS) of the gas being measured, and another of the calibration points (ABS) being a corresponding control-voltage signal pair for a reference measurement (REF), and defining a corresponding signal-control-voltage for the absorption value of the predefined gas being measured, forming a 'virtual' signal-control voltage sensitivity curve, with the aid of the calibration points formed using a reference gas, measuring absorption signal value(s) in the vicinity of the preselected absorption maximum (ABS) and/or minimum, in the presence of the gas being measured, forming ratio(s) of the absorption signal values of the gas being measured and the absorption signal values of the reference gas, and a control voltage value corresponding to at least one minimum or maximum is defined from the ratio(s), in which case, on the basis of wavelengths of the absorption minima or maxima of the gas being measured, the voltage sensitivity of the distance between the mirrors is defined unequivocally and corrections are made to FPI voltage values (Vabs, Vref).

2. A method according to claim 1, wherein the gas being measured is carbon dioxide $CO_2$.

3. A method according to claim 1, wherein the reference gas is nitrogen $N_2$.

4. A method according to claim 1, wherein the defining step is carried out automatically, in connection with starting of the Fabry-Perot interferometer.

5. A method according to claim 1, wherein the defining step is carried out at regular intervals in time.

6. A method according to claim 1, wherein the defining step is carried out after a specific number of measurements.

7. A method according to claim 1, wherein the defining step is carried out when a specific content condition of the measurement gas is met.

8. A method according to claim 1, wherein the defining step is carried out on the basis of a change in an external control factor.

9. A method according to claim 1, wherein the defining step is carried out whenever a user so wishes.

10. A method according to claim 1, wherein a limit condition is set for the content of the measurement gas.

11. A method according to claim 1, wherein a lower and/or upper limit is set for a magnitude of change in variables Vabs and Vref.

12. A method according to claim 1, wherein a multipoint reference curve is formed from the reference gas.

13. A method according to claim 1, wherein the method is used in connection with a short Fabry-Perot interferometer.

14. A method according to claim 1, wherein a corrected Vref value, corresponding to a corrected Vabs value, is calculated by deriving the connection between an FPI control voltage and a void interval from an equilibrium condition between an electrostatic force and a spring force of an upper one of the two mirrors.

15. A method according to claim 1, wherein a user is always given an error message in a situation requiring correction.

16. A method according to claim 1, wherein a control-voltage correction is made automatically.

17. A method according to claim 1, wherein the 'virtual' signal-control voltage sensitivity curve is a straight line formed with the aid of the calibration points formed using the reference gas.

18. A method according to claim 1, wherein the defining step is carried out on the basis of a change in environmental conditions.

19. A method according to claim 1, wherein a user is always given an error message in a situation requiring correction and an instruction to make a control-voltage correction.

* * * * *